United States Patent [19]
Maul et al.

[11] Patent Number: 4,801,763
[45] Date of Patent: Jan. 31, 1989

[54] SELECTIVE CHLORINATION OF CHLOROTRIFLUOROETHYLENE TELOMERS

[75] Inventors: James J. Maul; Bobby F. Dannels, both of Grand Island; David Y. Tang, East Amherst, all of N.Y.

[73] Assignee: Occidental Chemical Corporation, Niagara Falls, N.Y.

[21] Appl. No.: 78,327

[22] Filed: Jul. 27, 1987

[51] Int. Cl.$^4$ ............... C07C 17/20; C07C 17/38; C07C 19/08; C07G 13/00
[52] U.S. Cl. ............... 570/177; 204/157.95; 570/134; 570/137; 570/170; 570/178
[58] Field of Search ............... 570/178, 170, 177, 134, 570/137; 204/157.95

[56] References Cited

U.S. PATENT DOCUMENTS

| 2,788,375 | 4/1957 | Ehrenfeld | 204/157.95 |
| 3,558,723 | 1/1971 | Davis et al. | 570/170 |
| 3,686,082 | 8/1972 | Ruehlen | 204/157.95 |
| 4,731,170 | 3/1988 | Caporiccio et al. | 570/170 |

FOREIGN PATENT DOCUMENTS 1130063 10/1968 United Kingdom ............... 570/178

Primary Examiner—J. E. Evans
Attorney, Agent, or Firm—James F. Tao; William G. Gosz

[57] ABSTRACT

A process is disclosed for purifying and stabilizing a mixture of regular chlorotrifluoroethyelne telomers of formula $RCXCl(CF_2CFCl)_nBr$ from bromine-containing irregular telomer impurities of similar molecular weight. The telomer mixture is produced by reacting chlorotrifluoroethylene with a telogen of formula $RCXClBr$, where R is $CF_2Br$, or Cl, and X is Cl or F. The telomer mixture is then chlorinated using either elevated temperature alone (100° C.–350° C.), or a combination of elevated temperatures (100° C.–200° C.) and light energy primarily of the wavelength region greater than about 3000°A. Under these conditions, CFClBr telomer end group of the regular or normal telomer is chlorinated to form —$CFCl_2$ end groups, while the bromine-containing irregular telomer impurities (whose bromine-containing end groups are substantially only —$CF_2Br$) are substantially not chlorinated. The desired regular telomers can then be readily separated from the higher boiling impurities by distillation. Any —$CF_2Br$ groups present in the isolated regular telomer are then further stabilized by prolonged chlorination under the above conditions or at elevated temperatures (100° C.–350° C.) with irradiation by a UV lamp.

20 Claims, No Drawings

SELECTIVE CHLORINATION OF CHLOROTRIFLUOROETHYLENE TELOMERS

BACKGROUND OF THE INVENTION

The present invention relates to a free radical chlorination process for purifying and stabilizing bromine-containing chlorotrifluoroethylene telomers to prepare stable products for use in applications such as for non-flammable hydraulic fluids.

Various methods of preparing chlorotrifluoroethylene ("CTFE") telomers are known in the prior art and have been practiced commercially for many years. An article by William T. Miller, Jr. et al in *Industrial and Engineering Chemistry*, pages 333-337 (1947), entitled "Low Polymers of Chlorotrifluoroethylene", describes a process for producing low molecular weight polymers of CTFE by polymerization of CTFE in a solution of chloroform using benzoyl peroxide as a polymerization promoter. Other solvents disclosed in the reference as being useful for this purpose include carbon tetrachloride and tetrachloroethylene. The solution is heated in a pressure vessel for 1¾ hours at 100° C., and the unreacted CTFE monomer and chloroform are removed by distillation, leaving a crude telomer of general formula $CHCl_2(CF_2CClF)_nCl$, which can be further heated and distilled to yield products ranging from a light oil to a semi-solid wax or grease.

Another process for preparing low molecular weight CTFE polymers is described in U.S. Pat. No. 2,788,375, issued Apr. 9, 1957. This process involves reacting CTFE with a saturated brominated compound in the presence of a source of radiation. Suitable brominated compounds include bromotrichloromethane and 1,2-dibromo-2-chlorotrifluoroethane ($CF_2BrCClFBr$). The saturated bromopolychlorofluoro compounds obtained by this process are then distilled, and the isolated fractions reacted with chlorine in the presence of tungsten light, at 150° C. to 250° C., such as supplied by a tungsten filament lamp, to prepare the corresponding polychlorofluoro compounds. The process disclosed in this patent is not a selective chlorination process since it results in the chlorination of both the telomer species and the organic impurities, and therefore does not assist in the separation and purification of the telomer species.

It is therefore a principal object of the present invention to provide an improved process for purifying and stabilizing bromine-containing telomers which can be used as non-flammable hydraulic fluids.

SUMMARY OF THE INVENTION

In accordance with the present invention, a process for purifying and stabilizing a mixture of chlorotrifluoroethylene telomers of formula, $$RXCl(CF_2CFCl)_nBr$$

where
n is in the range of 1 to 10,
R is $CF_2Br$ or Cl and
X is Cl or F
and bromine containing isomeric telomer impurities of similar molecular weight generated during the telomerization reaction, comprises treating the mixture with $Cl_2$ at a temperature of from about 100° C. to about 350° C., or a temperature of from about 100° C. to about 200° C. in the presence of a suitable light source emitting energy primarily at a wavelength greater than about 3000 Å wave length. Temperatures of less than about 100° C. are generally not effective, while higher temperatures can result in chlorination of the impurities.

These conditions are suitable to readily effect the conversion of the —CFClBr end group of the regular telomer to a —$CFCl_2$ end group, but much less effective to chlorinate the bromine-containing organic impurities (whose bromine-containing end groups are substantially only —$CF_2Br$ groups). The resulting chlorinated normal telomers are lower boiling than the irregular bromine-containing telomer impurities and are separated from the impurities by techniques such as distillation.

The telomers of this invention are prepared by reacting chlorotrifluoroethylene with a telogen of the formula RCXClBr in the presence of a suitable catalyst. R and X are as defined above.

A suitable light source within the scope of this invention is a light source emitting energy having a wavelength primarily in the region greater than about 3000 Å, such as an incandescent tungsten light or more preferably black light.

The regular telomer is rendered more stable in the above step since the resulting —$CFCl_2$ end group is chemically and thermally more stable than the —CFClBr group.

After isolation of the regular telomer, if the regular telomer also contains a —$CF_2Br$ end group it can then be further chlorinated and stabilized by either prolonged treatment under the chlorination conditions described above, or treatment with $Cl_2$ gas at 100° C. to about 350° C. while irradiating with a UV energy source.

DESCRIPTION OF THE PREFERRED EMBODIMENTS

The telomers which can be purified and stabilized according to the process of the present invention are bromine-containing chlorotrifluoroethylene telomers which contain at least one end group of formula —CFClBr. Telomers of this general description can be prepared using a variety of procedures. For example, U.S. Pat. No. 2,788,375, issued Apr. 9, 1957, describes a photochemical process for reacting chlorotrifluoroethylene with various bromine-containing telogens, such as $CCl_3Br$ and $CF_2BrCClFBr$, to prepare bromine-containing polymers of various molecular weights. An alternate procedure for preparing bromine-containing chlorotrifluoroethylene telomers is described in a commonly assigned application Ser. No. 816,183, filed Jan. 6, 1986. This latter telomerization process employs a catalyst system comprising ferric chloride and a metal such as nickel to produce telomer intermediates which, after replacing bromine substitutents with chlorine, have properties which are particularly useful for formulating non-flammable hydraulic fluids.

In general terms, particularly desirable telomers for use in this invention can be advantageously prepared by reacting chlorotrifluoroethylene with a telogen of formula RCXClBr, where R is $CF_2Br$ or Cl and X is Cl or F. A solvent such as acetonitrile is employed and the reaction mixture includes a suitable catalyst. This process can be illustrated as follows:

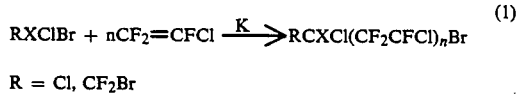

(1)

R = Cl, $CF_2Br$

X = Cl, F where n is in the range of 1 to 10.

In reaction (1), K designates a catalyst system which can comprise an alkali metal ferrocyanide such as potassium ferrocyanide, or a combination of ferric chloride and a suitable reducing agent such as benzoin or a metal selected from the group consisting of iron, nickel, cobalt, vanadium, molybdenum and chromiun, the preferred metal being nickel.

The principal products of reaction (1) are bromine-containing telomers of general formula $RCXCl(CF_2CFCl)_nBr$. These telomers contain the —CFClBr end group and are hereinafter referred to as "normal" or "regular" telomers. However, various other organic materials are also produced by this reaction in significant quantities, i.e. usually on the order of 5% to 10% by weight of product. Compounds which have been isolated and identified can be represented by the following formula:

$$RCClX(CF_2CFCl)_a\text{—}(CFClCF_2)_bBr \tag{2}$$

Major isomeric impurities of formula (2) contain —$CF_2Br$ end groups and are essentially analogs of the normal telomer described above both in terms of their structure and molecular weight ranges. Consequently, these isomers are very similar in terms of their physical and chemical properties to the telomers produced in reaction (1), and cannot be readily separated from these telomers. This is unfortunate since many commercial applications require a high degree of product stability. Under these circumstances, the isomers or "irregular" telomers must be removed from the reaction mixture.

It has now been found that the normal telomers prepared according to reaction (1) can be separated from the bromine-containing organic impurities such as (2) by (a) chlorinating the mixture of telomers and impurities
  i. at temperatures of from about 100° C. to about 350° C., or
  ii. at temperatures of from about 100° to about 200° C. in the presence of irradiation from a suitable light source emitting energy primarily at wavelengths greater than about 3000 Å, and (b) separating the regular chlorinated telomers from the impurities by conventional distillation procedures.

The chlorination conditions are suitable to effect the conversion of the —CFClBr telomer end groups to —$CFCl_2$ end groups, but not effective to chlorinate the bromine-containing irregular telomer organic impurities, e.g. those whose bromine-containing end groups are predominantly of the form —$CF_2Br$.

Operable sources of radiant energy for this purpose include incandescent tungsten lights, black light and the like which emit energy primarily in the wavelength regions above about 3000 Å, and preferably, primarily in the range of about 3000 Å to about 4000 Å. Surprisingly, general UV light sources which emit energy in the near, middle and far UV regions are less desirable under the reaction temperatures described since they result in the chlorination of both type functionalities (—$CF_2Br$ and —CFClBr). This makes the separation of the normal telomers from the impurities impractical.

The presence of UV light in the initial chlorination can introduce additional problems into the isolation of the pure regular telomers in high yields. In certain instances, where —Br is contained at each end of the telomer, higher molecular weight materials are formed during a UV radiated chlorination process. This can complicate the reaction process by increasing the viscosity of the reaction mixture, as well as by reducing the light transmittance of the reaction mixture, leading to higher molecular weight polymer formation.

An additional advantage is realized in the above-described chlorination. During the initial telomerization reaction some chlorine and/or bromine isomerizations of the original telogen may occur, for example, $$CF_2Br\text{—}CFClBr \rightarrow CF_2Cl\text{—}CFBr_2 \tag{3}$$

The telomerization product from that isomerized telogen is as follows, $$CF_2Cl\text{—}CFBr_2 + CTFE \rightarrow CF_2Cl\text{—}CFBr(CF_2\text{—}CFCl)_nBr \tag{4}$$

The chlorination and stabilization procedure of this invention also converts this material into regular bromine-free telomers.

$$CF_2Cl\text{—}CFBr(CF_2CFCl)_nBr \rightarrow CF_2Cl\text{—}CFCl\text{—}(CF_2CFCl)_nCl \tag{5}$$

Some commercial applications require separation of the telomer mixture into discrete telomers. Since the molecular weight distribution of the isomeric impurities correspond somewhat to the molecular weight distribution of the telomers, the separated telomers will contain similar quantities of these impurities, i.e. 5% to 10% by weight. The purification process of this invention can therefore be conveniently applied to telomers which have been previously fractionated to obtain discrete species, i.e. single n values. Alternatively, a telomer fraction containing a range of molecular weights, including the entire range of n values from 1 to 10, if desired, can be purified and subsequently separated into individual species to obtain essentially the same results.

In one embodiment of this invention, telomers of formula $CCl_3(CF_2CFCl)_nBr$ are prepared by reacting chlorotrifluoroethylene with $CCl_3Br$ in acetonitrile in the presence of a potassium ferrocyanide catalyst. This reaction can be illustrated as follows:

$$CCl_3Br + nCF_2\!\!=\!\!CFCl \xrightarrow{K_4Fe(CN)_6 \cdot 3H_2O} CCl_3(CF_2CFCl)_nBr \tag{6}$$

As shown in reaction (6), the telomers prepared according to this reaction have one —$CCl_3$ end group and one —CFClBr end group. The structure of these telomers, including the relative arrangement of the —$(CF_2CFCl)_n$— group and its components, has been confirmed by NMR spectroscopy.

Individual telomer species corresponding to discrete n values can then be isolated, if desired, and chlorinated in the presence of a black light radiation source as described above to replace the single bromine atom in the telomer with a chlorine atom, while leaving the impurities essentially uneffected. The telomer can then be separated from the impurities by distillation to prepare an essentially pure compound. Alternatively, the telomerization reaction mixture can be chlorinated as described above and the individual chlorinated species can then be isolated by distillation.

In another embodiment, telomers of formula $CF_2BrCFCl(CF_2CFCl)_nBr$ are prepared by reacting chlorotrifluoroethylene with $CF_2BrCFClBr$ in acetonitrile in the presence of a catalyst system comprising ferric chloride and a metal selected from the group consisting of iron, nickel, cobalt, vanadium, molybdenum and chromium, and preferably nickel This reaction can be illustrated as follows:

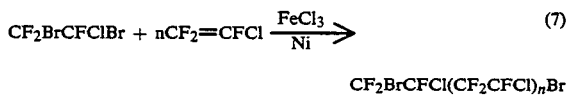

(7)

$$CF_2BrCFClBr + nCF_2=CFCl \xrightarrow[Ni]{FeCl_3} CF_2BrCFCl(CF_2CFCl)_nBr$$

The normal telomers prepared according to reaction (7) have one $-CF_2Br$ end group and one $-CFClBr$ end group. The structure of these particular telomers, including the relative arrangement of the $-(CF_2CFCl)_n-$ group and its components, has also been verified by NMR spectroscopy. This particular reaction, and the products obtained therefrom, are the subject of a commonly assigned U.S. patent application Ser. No. 816,183, filed Jan. 6, 1986.

The telomer can be purified before or after isolation of the individual telomer species corresponding to discrete n values. In the case of this reaction, however, it has been found advantageous to convert the $-CFClBr$ telomer end group into a $-CFCl_2$ end group by chlorinating the telomer as described above. Under these conditions, neither the $-CF_2Br$ telomer end group of the normal telomer nor other bromine-containing isomers are substantially chlorinated. However, the partially chlorinated telomer can be readily separated from the impurities by distillation at this stage. Upon separation, the purified normal telomer can then be further chlorinated, converting $-CF_2Br$ with $-CF_2Cl$ using a general UV lamp which emits roughly the same amount of energy in the near UV (3200 A to 4000 A), middle UV (2800 A to 3200 A), and far UV (2200 A to 2800 A) regions. The shorter wavelengths included in this band have a higher energy level and are therefore effective in chlorinating $-CF_2Br$ end groups which are more difficult to chlorinate.

There is an additional advantage to this sequential chlorination process. It has been found that if the above mixture of telomers is treated directly with UV light, then the reaction product is contaminated with isomers and to some degree with higher telomer formation as well. The latter is possibly a result of a combination of various radical alkyl fragments formed during UV radiation.

The final product is a fully chlorinated telomer which is sufficiently stabilized for commercial applications. If desirable, however, the telomer can be further fluorinated to improve its stability even more using conventional fluorinating agents such as chlorine trifluoride or hydrogen fluoride.

The chlorinating agent of choice in the practice of this invention is chlorine gas. Suitable chlorination reactions are conducted at temperatures in the range of from about 100° C. to about 200° C. Conventional equipment is used for photochlorination as well as distillation as will be readily appreciated by those skilled in this art.

The following examples are intended to further illustrate the various embodiments and advantages of the present invention, without limiting it thereby. These examples illustrate the purification of bromine-containing CTFE telomers using various telogens.

EXAMPLE 1

A mixture of telomers of formula $CCl_3(CF_2CFCl)_nBr$ and bromine-containing organic impurities was prepared by reacting chlorotrifluoroethylene with $CCl_3Br$ in the presence of a potassium ferrocyanide catalyst in a solution of acetonitrile. The reaction was conducted at a temperature of 100° C. under autogenous pressure.

The mixture was separated into individual telomer species, i.e. n=1,2,3,4 etc., using spinning band distillation. Boiling point data for each telomer species is indicated below:

| Telomer | Boiling Point |
| --- | --- |
| $CCl_3(CF_2CFCl)_1Br$ | 87° C. (at 50 mm Hg) |
| $CCl_3(CF_2CFCl)_2Br$ | 120° C. (at 24 mm Hg) |
| $CCl_3(CF_2CFCl)_3Br$ | 108° C. (at 0.15 mm Hg) |
| $CCl_3(CF_2CFCl)_4Br$ | 115° C. (at 0.13 mm Hg) |

The structure of each telomer was confirmed by GC/MS, which also confirmed the presence of bromine-containing isomeric impurities with each fraction.

The $CCl_3(CF_2CFCl)_2Br$ fraction (corresponding to an n value of 2) was heated to 150° C. and irradiated with black light while chlorine gas was bubbled into the stirred liquid. The progress of the reaction was monitored with GC, which indicated that the $CCl_3(CF_2CFCl)_2Br$ telomer reacted with chlorine and was converted to a telomer of formula $CCl_3(CF_2CFCl)_nCl$, while the isomeric impurities did not react with chlorine under these conditions.

The lower boiling chlorinated telomer was then separated from the higher boiling isomers by distillation. The boiling point of the chlorinated telomer (n=2) was measured as 130° C. at 52 mm Hg. The structure of this compound was confirmed by NMR and GC/MS.

The other fractions corresponding to n values of 1, 3 and 4 were each treated with chlorine gas at various temperatures while being irradiated with black light. The chlorination temperature, boiling point data and purity of the isolated telomers is indicated below:

| Telomer | Chlorine Temperature | Boiling Point | Purity |
| --- | --- | --- | --- |
| $CCl_3(CF_2CFCl)Cl$ | 100° C. | 149° C. (at 760 Torr) | 99.9% |
| $CCl_3(CF_2CFCl)_3Cl$ | 150° C. | 63° C. (at 0.09 Torr) | 99.9% |
| $CCl_3(CF_2CFCl)_4Cl$ | 160° C. | 110° C. (at 0.1 Torr) | 99.9% |

The structure of these compounds was confirmed by NMR and GC/MS.

EXAMPLE 2

A mixture of telomers of formula $CCl_3(CF_2CFCl)_nBr$ and bromine-containing organic impurities was prepared as described in Example 1. The mixture was washed with aqueous HCl and water, and then dried.

The mixture was then separated into a fraction containing the telomers and impurities corresponding to n values of 2, 3, 4 and 5. This fraction was treated with chlorine gas at a temperature of 160° C. in the presence of black light for 30 hours.

GLC indicated that all of the normal telomers had been converted to the corresponding chlorine form, i.e. $CCl_3(CF_2CFCl)_nCl$, while the isomeric impurities had not reacted.

The telomers were separated from the impurities and into individual species by distillation. The boiling points of the individual telomers corresponded to those of Example 1.

Examples 3 and 4 are comparative examples which illustrate the positive results obtained when chlorinating the telomer mixture in the presence of a black light energy source (Example 4) as contrasted to a general UV light source, or no light source (Example 3).

EXAMPLE 3

A 25 ml., 3-neck pyrex flask, fitted with a thermometer, a magnetic stirrer, and a water-cooled condenser, was connected to a source of chlorine and nitrogen through a 1/16" rotometer, and charged with 27 grams of a telomer fraction having the following composition:

| Component | Amount (%) |
| --- | --- |
| $CF_2BrCFCl(CF_2CFCl)_2Br$ | 91.6 |
| $CF_2BrCFCl(CF_2CFCl)_2Cl$ | 3.8 |
| Bromine-Containing Isomeric Impurity | 4.6 |

After heating the mixture to 185° C., chlorine was introduced into the reactor. After 45 minutes, a temperature of 192° C. was recorded. A sample of the mixture was removed and analyzed, and found to have the following composition:

| Component | Amount (%) |
| --- | --- |
| $CF_2BrCFCl(CF_2CFCl)_2Br$ | 88.8 |
| $CF_2BrCFCl(CF_2CFCl)_2Cl$ | 4.6 |
| Bromine-Containing Isomeric Impurity | 4.6 |

These results indicate that very little chlorination had been accomplished.

The reaction mixture was then irradiated using a 400 W medium pressure mercury vapor lamp. The temperature was maintained at 185° C. After 6.5 hours, the reaction was complete. The reaction mixture had the following composition:

| Component | Amount (%) |
| --- | --- |
| $CF_2Br CFCl(CF_2CFCl)_2Br$ | 0.0 |
| $CF_2BrCFCl(CF_2CFCl)_2Cl$ | 88.2 |
| $CF_2ClCFCl(CF_2CFCl)_2Cl$ | 7.6 |
| Bromine-Containing Isomeric Impurity | 3.3 |
| Chlorinated Isomeric Impurity | 0.9 |

These results indicate that in addition to the desired chlorination of the —CFClBr group of the normal telomer, a substantial portion of the —CF₂Br groups of the undesirable isomeric impurity had also been chorinated.

EXAMPLE 4

A 100 ml., 3-neck pyrex flask, fitted with a magnetic stirrer, a thermometer, and a water-cooled condenser, was attached to a source of chlorine and nitrogen, and charged with 119 grams of a telomer fraction having the following analysis by GC:

| Component | Amount (%) |
| --- | --- |
| $CF_2BrCFCl(CF_2CFCl)_3Br$ | 92.9 |
| Bromine-Containing Isomeric Impurity | 7.1 |

After heating to 175° C., chlorine was introduced and the mixture was irradiated with a 15 W black fluorescent lamp. After 7.75 hours, the reaction was stopped. The product was analyzed and found to contain the following components:

| Component | Amount (%) |
| --- | --- |
| $CF_2BrCFCl(CF_2CFCl)_3Cl$ | 89.7 |
| $CF_2BrCFCl(CF_2CFCl)_3Br$ | 2.8 |
| $CF_2ClCFCl(CF_2CFCl)_3Cl$ | 0.9 |
| Bromine-Containing Isomeric Impurity | 6.3 |
| Chlorinated Isomeric Impurity | 0.3 |

The product was washed with a sodium thiosulfate solution, and then with water. It was then distilled on a spinning band still to obtain the telomer of formula $CF_2BrCFCl(CF_2CFCl)_3Cl$ in 99.3% purity. The product contained only 0.7% of isomers, and no other components.

EXAMPLE 5

A quartz flask was charged with 30.0 g. of a starting mixture which was contaminated with substantial quantities of bromine-containing isomer. Chlorine gas was bubbled into the liquid while it was irradiated with a 15 watt fluoroescent black lamp and maintained at increasing temperatures for different periods of time. The composition of the reaction mixture was monitored via GLC.

| | Starting Mixture | 100° C. 4 Hrs. | 120° C. 4 Hrs. | 150° C. 2 Hrs. | 175° C. 2 Hrs. | 200° C. 2 Hrs. |
| --- | --- | --- | --- | --- | --- | --- |
| $Br(CF_2CFCl)_4Br$ | 80.4 | 74.0 | 70.2 | 63.3 | 42.4 | 6.8 |
| Brominated Isomer | 7.5 | 6.5 | 6.4 | 6.5 | 7.0 | 6.9 |
| $Br(CF_2CFCl)_4Cl$ | 8.4 | 14.8 | 18.3 | 25.3 | 46.0 | 81.7 |
| Isomer | Trace | 0.6 | 0.1 | Trace | Trace | Trace |
| $Cl(CF_2CFCl)_4Cl$ | 0 | 0 | 0 | | Trace | 1.2 |
| Isomer | 0 | 0 | 0 | | Trace | Trace |

The above data indicates that in the presence of black light at temperatures of up to about 200° C., the normal telomer is selectively chlorinated at the —CFClBr end of the molecule. The normal telomer, $Br(CF_2CFCl)_4Cl$, is then isolated by distillation.

EXAMPLE 6

A quartz flask was charged with 30.2 g. of a starting mixture which was contaminated with substantial quantities of bromine-containing isomer. Chlorine gas was bubbled into the liquid while it was irradiated with a 100 watt incandescent tungsten lamp and maintained at increasing temperatures for 4-hour periods. The composition of the reaction mixture was monitored by GLC.

|  | Starting Mixture | 100° C. 4 Hrs. | 120° C. 4 Hrs. | 150° C. 4 Hrs. | 200° C. 4 Hrs. |
|---|---|---|---|---|---|
| Br(CF$_2$CFCl)$_4$Br | 80.4 | 77.3 | 35.3 | 9.5 | 0 |
| Brominated Isomer | 7.5 | 7.7 | 7.9 | 8.4 | 4.6 |
| Br(CF$_2$CFCl)$_4$Cl | 8.4 | 12.4 | 35.3 | 78.7 | 78.5 |
| Isomer | Trace | 0 | 0 | Trace | 2.24 |
| Cl(CF$_2$CFCl)$_4$Cl | 0 | 0 | 0 | 0.6 | 12.02 |
| Isomer | 0 | 0 | 0 | Trace | 0 |

The above data indicates that in the presence of tungsten at temperatures below about 175° C., the normal telomer is selectively chlorinated at the —CFClBr end of the molecule. The normal telomer, Br(CF$_2$CFCl)$_4$Cl, is then isolated by distillation.

EXAMPLE 7

A telomer mixture was prepared as described above from CCl$_3$Br and CF$_2$CFCl using KFe(CN)$_6$ as the catalyst. The seven-carbon fraction was isolated by spinning band distillation (assay below). Chlorine gas was bubbled into 258.22 g (0.47 Mole) of this mixture for 16.3 hours while the reaction mixture was irradiated with a fluorescent black lamp and the temperature was maintained at 130°–160° C. This material (229.9 g, 0.46 Moles, 97% yield) was then distilled to yield the desired seven-carbon product in 99+% purity (bp 67° C./0.08 mm).

|  | C-7-Br Fraction | After Chlorination |
|---|---|---|
| CCl$_3$(CF$_2$CFCl)$_3$Br | 92.28% | 3.65% |
| Bromine Containing Isomers | 6.58% | 5.50% |
| CCl$_3$(CF$_2$CFCl)$_3$Cl | 0.00% | 89.52% |

EXAMPLE 8

A mixture of telomers (21.2 g) of Br(CF$_2$CFCl)$_n$Br where n=2 to 6 where vaporized and passed along with gaseous chlorine twice through a nickel column preheated to 350° C. The column was 60 inches long and 1 inch in diameter.

The flow rates were as follows:

| Telomer Mixture | 0.3 g per Min. |
|---|---|
| Cl$_2$ | 100 cc per Min. |

The residence time for each of the passes was calculated to be 115 seconds. The starting material and product were assayed via GLC, and the area counts are presented below. The product recovered weighed 16.2 grams.

|  | Starting Material | After Pass #2 |
|---|---|---|
| Br(CF$_2$CFCl)$_2$Cl | 0.5 | 20.5 |
| isomer impurity | 0.0 | 0.0 |
| Br(CF$_2$CFCl)$_2$Br | 25.8 | 2.4 |
| n = 2 impurity | 0.5 | 0.3 |
| Br(CF$_2$CFCl)$_3$Cl | 1.6 | 31.9 |
| isomer impurity | 0.0 | 0.0 |
| Br(CF$_2$CFCl)$_3$Br | 30.4 | 2.3 |
| n = 3 impurity | 1.5 | 1.2 |
| Br(CF$_2$CFCl)$_4$Cl | 1.3 | 18.2 |
| isomer impurity | 0.0 | 0.0 |
| Br(CF$_2$CFCl)$_4$Br | 18.5 | 1.3 |
| n = 4 impurity | 1.1 | 0.7 |

-continued

|  | Starting Material | After Pass #2 |
|---|---|---|
| Br(CF$_2$CFCl)$_5$Cl | 0.8 | 7.0 |
| isomer impurity | 0.0 | 0.0 |
| Br(CF$_2$CFCl)$_5$Br | 9.4 | 0.5 |
| n = 5 impurity | 0.7 |  |

The above analyses indicate that the bromine atom on the —CFClBr group of the normal telomer was selectively being replaced by Cl. After further recycles of this vapor phase chlorination, the desired normal telomers Br(CF$_2$CFCl)$_n$Cl are separated by distillation from the respective higher boiling non-chlorinated bromine-containing isomeric impurities.

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A process for purifying a mixture of chlorotrifluoroethylene telomers from bromine-containing organic impurities, each of said chlorotrifluoroethylene telomers having an end group of formula —CFClBr, said process comprising the steps of:
   (a) chlorinating the mixture at a temperature in the range of about 100° C. to about 350° C. for a sufficient period of time to convert the —CFClBr telomer end groups into —CFCl$_2$ end groups, without chlorinating the bromine-containing organic impurities, and
   (b) separating the chlorinated telomers from the bromine-containing organic impurities.

2. The process of claim 1 wherein the chlorination reaction is conducted at a temperature in the range of about 100° C. to about 200° C. in the presence of a light source emitting energy primarily of a wavelength above about 3000 Å.

3. The process of claim 2 wherein the light source emits energy primarily having a wavelength in the region of from about 3000 Å to about 4000 Å.

4. The process of claim 1 wherein the telomers have the formula RCXCl(CF$_2$CFCl)$_n$Br, where n is in the range of 1 to 10, R is CF$_2$Br or Cl, and X is Cl or F.

5. The process of claim 4 wherein the chlorotrifluoroethylene telomers have the formula CCl$_3$(CF$_2$CFCl)$_n$Br, where n is in the range of 1 to 10.

6. The process of claim 4 wherein the chlorotrifluoroethylene telomers have the formula CF$_2$BrCFCl(CFCl)$_n$Br, where n is in the range of 1 to 10.

7. The process of claim 1 wherein the mixture of chlorotrifluoroethylene telomers and bromine-containing organic impurities is prepared by reacting chlorotrifluoroethylene with a telogen of formula RCXClBr, where R is CF$_2$Br or Cl, and X is Cl or F, in the presence of a catalyst, said reaction being conducted in a common solvent for the reactants and catalyst.

8. The process of claim 7 wherein the telogen is CCl$_3$Br.

9. The process of claim 8 wherein the catalyst is potassium ferrocyanide.

10. The process of claim 9 wherein the solvent is acetonitrile.

11. The process of claim 7 wherein the telogen is $CF_2BrCFClBr$.

12. The process of claim 11 wherein the catalyst comprises $FeCl_3$ and a metal selected from the group consisting of iron, nickel, cobalt, vanadium, molybdenum and chromium.

13. The process of claim 12 wherein the metal is nickel.

14. The process of claim 13 wherein the solvent is acetonitrile.

15. The process of claim 1 wherein the chlorinating agent is chlorine.

16. The process of claim 1 wherein the separated telomers are fluorinated to improve their stability.

17. A process for purifying and stabilizing chlorotrifluoroethylene telomers comprising the steps of:
 (a) reacting chlorotrifluoroethylene with 1,2-dibromo-2-chlorotrifluoroethylene in a solution of acetonitrile in the presence of a catalytic amount of ferric chloride and nickel, to prepare a mixture of dibrominated telomers of formula $CF_2BrCFCl(CF_2CFCl)_nBr$, where n is in the range of 1 to 10, and bromine-containing organic impurities,
 (b) chlorinating the mixture at a temperature in the range of about 100° C. to about 350° C. for a sufficient period of time to convert the dibrominated telomers into monobrominated telomers of formula $CF_2BrCFCl(CF_2CFCl)_nCl$, without chlorinating the bromine-containing organic impurities,
 (c) separating the monobrominated telomers from the bromine-containing organic impurities, and
 (d) chlorinating the monobrominated telomers in the presence of a second light source emitting energy of a wavelength which is effective to convert the monobrominated telomers into telomers of formula $CF_2ClCFCl(CF_2CFCl)_nCl$.

18. The process of claim 17 wherein the chlorination reaction is conducted at a temperature in the range of about 100° C. to about 200° C. in the presence of a light source emitting energy primarily of a wavelength above about 3000 Å.

19. The process of claim 18 wherein said first light source only emits energy of a wavelength in the region of from about 3000 Å to about 4000 Å, and the second light source is a general UV source.

20. The process of claim 17 wherein the chlorinating agent is chlorine.

* * * * *